United States Patent [19]

Kawai et al.

[11] Patent Number: 5,005,975
[45] Date of Patent: Apr. 9, 1991

[54] SURFACE PROFILE ANALYZER

[75] Inventors: Michio Kawai, Funabashi; Sadahiro Tanaka, Yokohama; Osamu Osanai, Chiba, all of Japan

[73] Assignee: Kao Corporation, Tokyo, Japan

[21] Appl. No.: 239,118

[22] Filed: Aug. 31, 1988

[30] Foreign Application Priority Data

Aug. 31, 1987 [JP] Japan .................................. 62-216773

[51] Int. Cl.⁵ ...................... G01N 21/00; G01B 11/30
[52] U.S. Cl. ...................................... 356/237; 356/371
[58] Field of Search .............. 356/371, 237, 241, 376; 250/562, 563, 572; 358/244, 76, 296

[56] References Cited

U.S. PATENT DOCUMENTS

| | | | |
|---|---|---|---|
| 3,439,988 | 4/1969 | Breske | 356/237 |
| 4,028,728 | 6/1977 | Sharp | 356/237 |
| 4,184,175 | 1/1980 | Mullane, Jr. | 356/237 |
| 4,449,818 | 5/1984 | Yamaguchi et al. | 356/371 |
| 4,736,245 | 4/1988 | Seto et al. | 358/76 |

*Primary Examiner*—Richard A. Rosenberger
*Assistant Examiner*—Hoa Pham

[57] ABSTRACT

A surface profile analyzer of the present invention is a device chiefly for analyzing the profile of the skin surface of a human. It has a ring-shaped illuminating device for irradiating a predetermined place of a test surface from all peripheral directions thereof, and an image pick-up device for photographing the test surface illuminated by the ring-shaped illuminating device. A digital signal generating device for converting the image signal of the test surface coming from the image pick-up device into a digital signal is used in conjunction with a computer to analyze the surface profile.

11 Claims, 3 Drawing Sheets

0
SURFACE PROFILE ANALYZER

BACKGROUND OF THE INVENTION

1. Field of the Invention

This present invention relates to a surface profile analyzer and more particularly to a surface profile analyzer for analyzing and evaluating the surface profile of a fine surface configuration, etc. in various soft or hard surfaces such as skin surface of a human body, fiber surface, floppy disk surface, cup surface, dish surface, etc.

2. Description of the Prior Art

Heretofore, in order to examine the profile of the skin surface, light is irradiated to the skin from one direction. The skin is directly photographed in its enlarged scale and then the profile of the skin is observed as disclosed, for example, in Japanese Patent Application Early Laid-open Publication No. Sho. 60-198130 and Japanese Utility Model Publication No. Sho. 62-24271. In order to obtain a much clear image of a skin surface, a replica of the skin surface is prepared (for example, GC-SUR-FLEX-F or SHIKA KOGYO KABUSHIKI KAISAA). An irregular image of the skin surface is transferred to an opaque substance and then the transferred image is enlarged by a stereomicroscope or the like and observed by either a microscope is attached with a video camera, A-D converter and a computer so as to analyze the surface surface state (as disclosed, for example, in Japanese Patent Application Early Laid-open Publication No. Sho 60-53121).

However, when using a stereomicroscope, since the skin surfaces of the yellow and white colored people are high in transparency, it is difficult to uniformly observe, detect and/or analyze the skin's furrow laid across the skin surface. On the other hand, when using a microscope or computer since the skin surface is indirectly observed by replication, shortcomings such reduced accuracy, much time and labor for preparing the replication and an unpleasant feeling for the person-to-be-tested during the making of the replication are realized.

The present invention has been developed to overcome the above-mentioned shortcomings.

SUMMARY OF THE INVENTION

It is therefore an object of the present invention to provide a surface profile analyzer, in which fine and delicate structure of a skin surface can be directly and accurately observed, detected and/or analyzed in a comparatively short period of time.

Another object of the present invention is to provide a surface profile analyzer which is capable of analyzing not only the skin surface but also various surfaces such as fiber surface, floppy disk surface, dish surface, plate surface, etc.

The present invention has been developed to achieve the above objects. As a result, the present invention can evaluate the largeness of the skin furrow, length and direction thereof, and area distribution of a skin ridge surrounding with the skin furrow and form evaluation can be very accurately by irradiating light to a predetermined portion of the skin surface from its all peripheral directions, producing a picture thereof, converting the image signal into a digital signal by an A-D converter and observing the digital signal through a computer. A surface profile analyzer according to the present invention comprises a ring-shaped illuminating device, an image pick-up device for photographing a test surface illuminated by the ring-shaped illuminating device, a digital signal generating device for converting an image signal of the test surface coming from the image pick-up device to a digital signal representing an image of the test surface and a computer (information processing device) which includes memory means for storing the digital signal, calculating means thereof and control means for controlling thereof.

DETAILED DESCRIPTION OF THE EMBODIMENT

A surface profile analyzer embodying the present invention will be described below with reference to the accompanying drawings.

Figure 1:
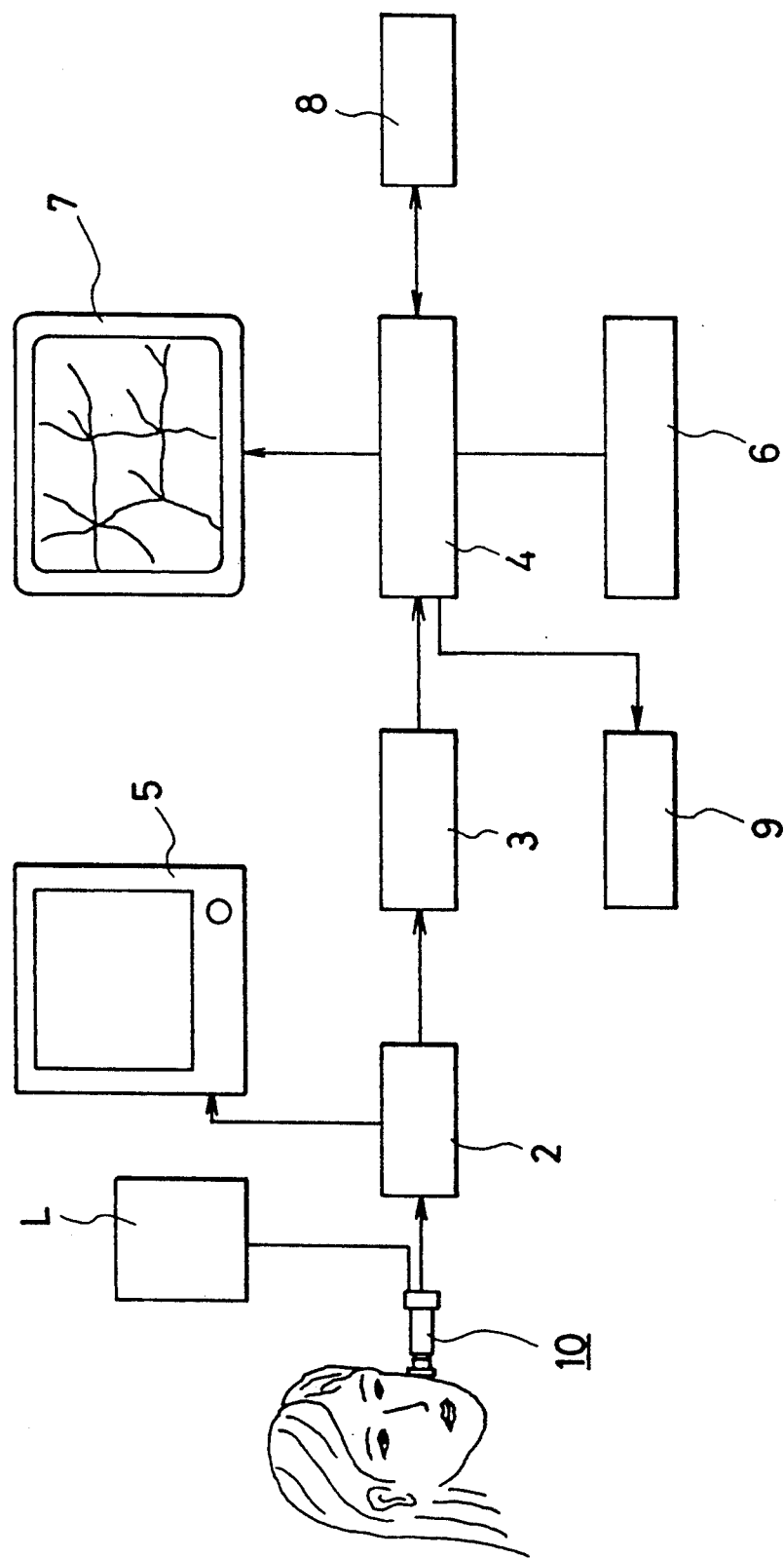
FIG. 1 is a block diagram showing the outline of one embodiment of the present invention together with its using mode.
Figure 2:
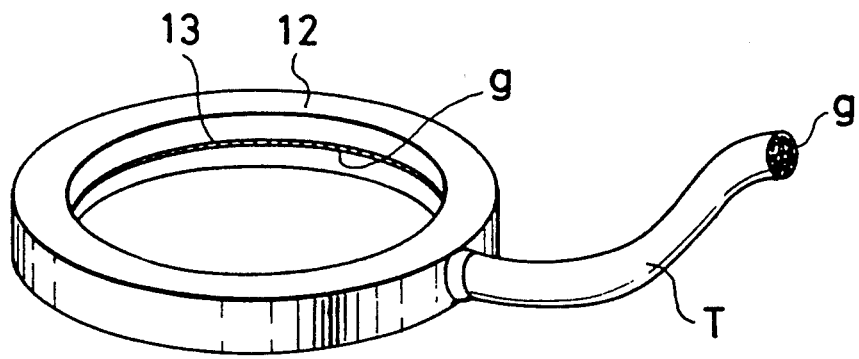
FIG. 2 is a perspective view showing one example of the ring-shaped illuminating device.

In FIG. 1, 10 denotes a small type video camera (a color or monochromatic vision camera, a CCD camera, etc. can be used) including a ring-shaped illuminating device 1 and an enlarging objective lens system 11, as shown in FIG. 2. In the video camera 10, a predetermined portion of a test surface can be irradiated from the all peripheral directions by the ringshaped illuminating device 1 of FIG. 2. The illuminated test surface image is enlarged by the enlarging objective lens system 11 of FIG. 2 and then photographed by the small type video camera 10.

The present invention also includes a negative-positive converter 2, an A-D converter 3 which constitutes a digital signal generating device, and a computer 4. The negative-positive converter 2 converts an image signal from .the small type video camera 10 thereby to clarify the skin furrow, etc. The converted image signal is converted to a digital signal by the A-D converter 3 and then inputted into the computer 4.

In one embodiment of the present invention, the image signal is converted by the negative-positive converter 2. However, the image signal from the small type video camera 10 may be converted into a digital signal by the A-D converter 3 without being converted. The image signal can be displayed on a TV monitor 5 without being converted or after being converted.

The computer 4 is provided with an image processing unit which includes a device for storing the digital signal, a calculating device thereof, and a control device thereof. An image of the inputted digital signal can be visually observed by the video monitor 7. The digital signal is calculated in binary, for example, in order to obtain the enlarge of the skin furrow, length and direction thereof, and the area distribution surrounding the skin furrow and shape evaluation (e.g., aspect ratio). At this time, a signal which is to be inputted into the computer 4 or a signal which has been subjected to calculation is stored in an outside memory 8, so that an image of other test surface can be compared according to necessity. An image displayed on the video monitor 7 can be printed by a printer 9. If the video monitor 7 is designed as such that it can display, for example, a quarter image, images of different test surface such as, for example, images of the skin surfaces of women of different ages can be compared relatively easily and correctly.

Figure 3:
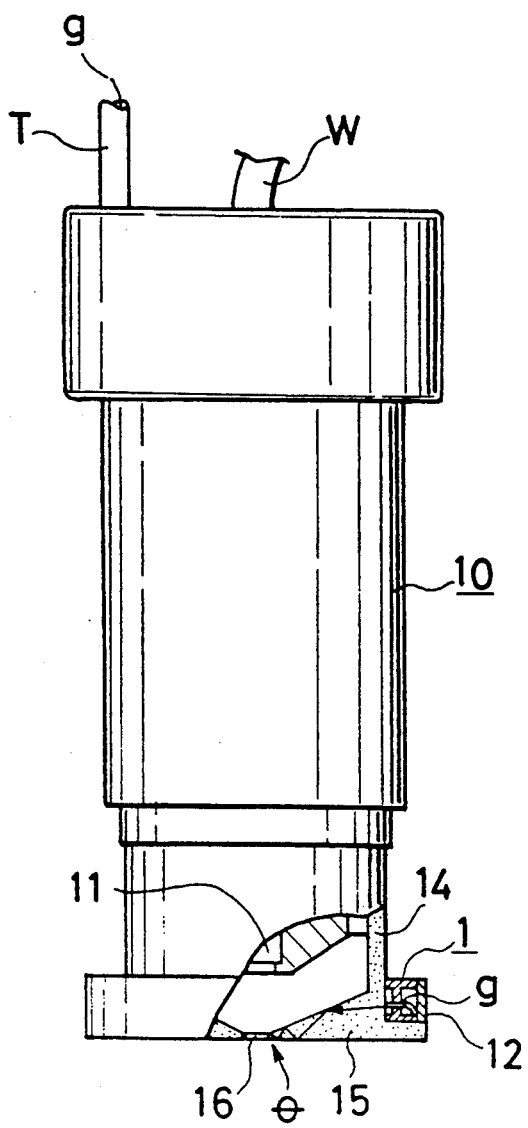
FIG. 3 is a partly cut-away side view of one example of a small type video camera including the ring-shaped illuminating device.

The ring-shaped illuminating device 1 used in the above embodiment will be described together with the small type video camera 10 equipped with the ring-shaped illuminating device 1. In the ring-shaped illuminating device 1, a bundle of optical fibers g, as shown in FIG. 2, are fitted into a circular optical fiber fitting body 12. Each optical fiber g within the bundle of the optical fibers g is exposed in an annular groove 13 continuously formed in the inner surface of the fitting body 12, as shown in FIG. 3, so that the tips of the optical fibers g are directed toward the center of the fitting body 12. The bundle of the optical fibers g are lead out through a tube T a light source L. 14 denotes a light guiding cylindrical body mounted on a foremost end portion (the lower end portion in FIG. 3) of the small type video camera 10 through the enlarging objective lens system 11. The cylindrical body 14 can be made by ejection molding with a transparent acrylic resin, the height of which is designed as such that its lower end face position becomes the focal point by the magnifying power of the enlarging objective lens system 11, etc. A flange is provided to the outer part of the lower end of the cylindrical body 14, and a tapered light guiding portion 15 which becomes thinner as it goes toward the center is integrally formed at the inner part thereof. The central portion is an observing hole portion 16 having a predetermined diameter.

The enlarging objective lens system 11 may be selectively used a suitable one which is capable of enlarging the object in a size easy to analyze the test surface depending on the kind of the test surfaces. The enlarging objective lens system 11 is threadedly engaged in an opening at the front end of the cylindrical body 14 so that the focal point is brought to the test surface when the observing hole portion 16 is abutted against the test surface. Therefore, the enlarging objective lens system 11 can be well focussed on a suitable place of the test surface according to necessity.

Figure 4:
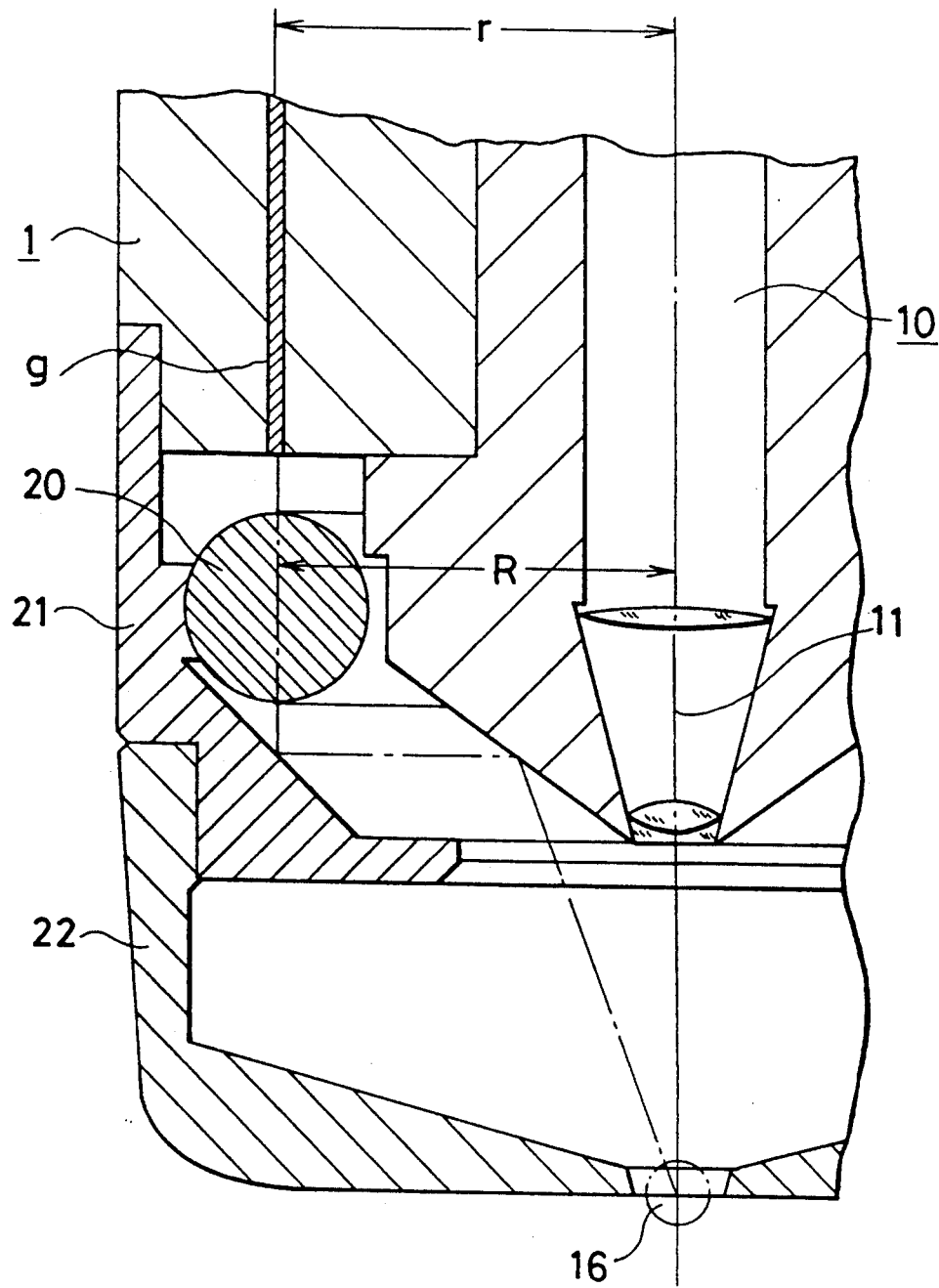
FIG. 4 is a vertical sectional view showing another example of the small sized video camera which includes the ring-shaped illuminating device.

The ring-shaped illuminating device 1 is fitted on the flange of the cylindrical body 14 and is secured thereto by suitable means such as a machine screw according to necessity. The light irradiated from the optical fiber g advances toward the center while repeating the reflection within the light guiding portion 15 as shown, for example, by the arrow in FIG. 3 or in FIG. 4, one dotted claim line reaches the observing hole portion 16 and illuminates the test surface, which is abutted against the observing hole portion 16, from its all peripheral directions.

The ring-shaped illuminating device 1, in the event the test surface is a skin surface, is located in a suitable position from where it can irradiate the skin surface at a low angle with respect to the skin's surface, such as 5 to 10°, see 0 in FIG. 3. Due to the foregoing arrangement, the amount of reflection light from the skin surface can be reduced and the detecting ability of the irregular image of the skin surface can be increased. It is preferable that the light source is provided with an infrared ray cut filter so that light having an infrared composition cut is irradiated to the test surface because the detecting ability of the irregular image of the test surface can be increased.

The light source L is not particularly limited. For example, a halogen lamp, a xenon and a tungsten lamp of a color temperature 3000° K., 30W may be used as the light source L. Similarly, the optical fiber g is not limited its diameter nor the size of its bundle. For example, a bundle of optical fibers, in which the diameter of each fiber is 50um and the diameter of the bundle is approximately 5mm can be used. The enlarging objective lens system 11 has a long focal point depth, preferably from 100 to 400 magnifying powers and more preferably from 100 to 300 magnifying powers.

The ring-shaped illuminating device 1 is not particularly limited in its configuration, structure, etc. as long as it is capable of illuminating a predetermined place of the test surface from its all peripheral directions. For example, a ring-shaped illuminating device shown in FIG. 4 may be used. The ring-shaped illuminating device of FIG. 4 will be briefly described. The ring-shaped illuminating device 1 is attached to the outer periphery of the small type video camera 10 over the entire length thereof. The optical fibers g extend toward the lower end of the ring-shaped illuminating device 1 as such that the lower ends thereof form a circular shape coaxial with the optical axis of the small type video camera 10 and so that the optical fibers g face the same direction as the optical axis. The optical fibers 9 serve as a circular light irradiating end.

In the vicinity of the front surface of the irradiating end of the optical fibers g of the ring-shaped illuminating device 1, a ring-shaped lens 20 is located. The overall configuration of the ring-shaped lens 20 is annular and its diameter section is a circle. The radius r of a circle formed by connecting the center of the sectional circle is identical with the radius R of the irradiating foremost end circle. Since it is continuously connected thereto with a distance of ⅔ of the radius of the sectional circle separated from the irradiating foremost end circle, the light irradiated from the ring-shaped illuminating device 1 passes through the ring-shaped lens 20 and converged into a conical surface shape.

Disposed in front of the ring-shaped lens 20 (a lower position in the figure) is a holding frame 21 for holding the ring-shaped lens 20 having a conical specular surface with its inner surface inclined at 45° with respect to the direction of the optical axis and threaded secured to the lower end of the ring-shaped illuminating device 1. The converged light is reflected in the horizontal direction by the specular surface. The reflecting light is reflected again by a conical outside surface having an angle of 55° with respect to the optical axis of a frame for holding the enlarging objective lens 11 of the small type video camera 10, reaches the observing hole portion 16 shown by a tiny circle and uniformly and brightly illuminates the hole portion 16 from all peripheral directions having an angle of 20° with respect to the optical axis. Out of the compositions of light which is diffusedly irradiated from the optical fibers g, an optical path of the light which is irradiated in the direction of the optical axis is shown by one dotted chain line. 22 denotes a spacer threadedly secured to one side of the holding frame 21. The lower end face of the spacer 22 is in the same distance position with the field.

Next, the use of the illustrated apparatus in FIGS. 1 through 3 will be described with reference to FIG. 1 in which the apparatus is used for analyzing the skin surface of a human body.

Firstly, the observing hole portion 16 of the small type video camera 10, as shown in FIG. 1, is abutted against the skin surface of an object-to-be-analyzed. Light coming from the light source L is guided through the optical fibers g of the ring-shaped illuminating device 1 and irradiated from the foremost ends thereof. As a result, the irradiating light passes through the light guiding portion 15 and illuminates the skin surface from all peripheral directions thereof. The illuminated skin surface image is enlarged by the enlarging objective lens 11 and then photographed by the small type video camera 10.

Nextly, an image signal of the skin surface photographed by the small type video camera 10 is transmitted to the negative-positive converter 2 through the cable W and converted by the negative-positive converter 2. As a result, the skin furrow, etc. of the skin surface is made clearer. The converted image signal is converted to a digital signal by the A-D converter 3 and then inputted into the computer 4. At this time, by having the TV monitor 5 display the image signal from the small type video camera 10, the place of the skin test surface can be changed and focussing can be performed.

The image of the digital signal input into the computer 4 can be visually observed by naked eye through the video monitor 7. In the computer 4, the digital signal is calculated in binary using the data which has been input in the image processing unit 6 beforehand in order to obtain the largeness of the skin furrow, length and direction thereof, and the area distribution surrounding by the skin furrow and shape evaluation (e.g., aspect ratio).

A test example using a surface profile analyzer according to the present invention will now be described in order to concretely show the effects of the invention.

Test Example

The profile of the surfaces of the cheek portions of women of the ages of 18, 36 and 54 was analyzed using the surface profile analyzer of the present invention shown in FIGS. 1 through 3. The results are shown in the following table.

| AGE | TOTAL LENGTH OF SKIN GROOVE (mm) | AVERAGE AREA OF SKIN HILL (mm) | SKIN HILL |
| --- | --- | --- | --- |
| 18 | 10.56 | 0.035 | SMALL, UNIFORM AREA |
| 36 | 7.42 | 0.063 | MEDIUM, SLIGHTLY IRREGULAR AREA |
| 54 | 4.32 | 0.15 | LARGE, IRREGULAR AREA |

[Note]
(1) In the above table, the total length of the skin furrow and the average area of the skin ridge are values calculated based on the results of the observation of the binary image shown by the video monitor, the evaluation of the skin ridge is based on the naked eye observation of the negative-positive converting image displayed by the TV monitor.
(2) The binary image displayed by the video monitor is an enlarged image of the skin surface of 1.2.mm$^2$ (square millimeters).
(3) The terms small, medium and large shown in the column of the skin ridge are relative evaluation.

(1) In the above table, the total length of the skin furrow and the average area of the skin ridge are values calculated based on the results of the observation of the binary image shown by the video monitor, the evaluation of the skin ridge is based on the naked eye observation of the negative-positive converting image displayed by the TV monitor. (2) The binary image displayed by the video monitor is an enlarged image of the skin surface of 1.2 mm$^2$ (square millimeters) (3) The terms small, medium and large shown in the column of the skin ridge are relative evaluation.

While the embodiment and application of the present invention have been shown and described, it would be apparent to those skilled in the art that many more modifications are possible without departing from the inventive concepts herein. The present invention, therefore, is not to be restricted except inn the spirit of the appended claims.

What is claimed is:

1. A profile analyzer for human skin surfaces comprising:
   a ring-shaped illuminating device for irradiating a predetermined area of a human skin surface from all peripheral directions thereof at an irradiating angle of 0° to 10° with respect to the skin surface;
   image pick-up means for photographing the skin surface illuminated by said ring-shaped illuminating device, thereby generating an image signal;
   negative-positive converter means, operatively connected to said image pick-up means, for converting said image signal representing the skin surface to from a negative image to a positive image;
   digital signal generating means, operatively connected to said negative-positive converter means, for converting said image signal representing a positive image of skin surface into a digital signal representing an image of the skin surface; and
   a computer including member means for storing said digital signal.

2. profile analyzer as claimed in claim 1, wherein said irradiating angle of said ring-shaped illuminating device is from 5° to 10° with respect to the skin surface.

3. A surface profile analyzer comprising:
   illuminating means for irradiating a predetermined area of a test surface from all peripheral directions thereof at an irradiating angle of 0° to 10° with respect to the test surface;
   image signal generating means for generating an image signal representing an image of said predetermined area of the test surface; and
   processing means, operatively connected to said image signal means, for processing said image signal into information to be analyzed by an operator;
   said image signal generating means includes negative to positive converter means for converting said image signal representing said image of said predetermined area from a negative image to a positive image.

4. The analyzer as claimed in claim 3, wherein said illuminating means is ring-shaped.

5. The analyzer as claimed in claim 3, wherein said illuminating means includes optical fibers to cause radiation from all peripheral directions.

6. The analyzer as claimed in claim 3, wherein said angle of irradiation is 5° to 10°.

7. The analyzer as claimed in claim 3, wherein the test surface is human skin.

8. The analyzer as claimed in claim 3, wherein the test surface is a fiber surface.

9. The analyzer as claimed in claim 3, wherein the test surface is a floppy disk surface.

10. The analyzer as claimed in claim 3, wherein the test surface is a disk surface.

11. The analyzer as claimed in claim 3, wherein the test surface is a plate surface.

* * * * *